United States Patent
Frericks et al.

(10) Patent No.: US 7,421,299 B2
(45) Date of Patent: Sep. 2, 2008

(54) STIMULATION ELECTRODE AND METHODS OF MAKING AND USING SAME

(75) Inventors: Matthias Frericks, Hanau (DE); Oliver Keitel, Aschaffenburg (DE); Frank Krüger, Bruchköbel (DE); Heiko Specht, Aschaffenburg (DE); Hans-Jürgen Wachter, Rödermark (DE); Christiane Leitold, Wölfersheim (DE)

(73) Assignee: W.C. Heraeus GmbH & Co. KG, Hanau (DE)

( * ) Notice: Subject to any disclaimer, the term of this patent is extended or adjusted under 35 U.S.C. 154(b) by 260 days.

(21) Appl. No.: 10/735,069

(22) Filed: Dec. 12, 2003

(65) Prior Publication Data

US 2004/0127966 A1    Jul. 1, 2004

(30) Foreign Application Priority Data

Dec. 13, 2002    (DE) ............... 102 58 651

(51) Int. Cl.
*A61N 1/00*    (2006.01)
(52) U.S. Cl. .................. 607/116
(58) Field of Classification Search ........ 607/121–122, 607/119, 116; 600/310
See application file for complete search history.

(56) References Cited

U.S. PATENT DOCUMENTS

| | | | | |
|---|---|---|---|---|
| 4,156,429 A | * | 5/1979 | Amundson | 607/121 |
| 4,440,178 A | * | 4/1984 | Bussard et al. | 607/121 |
| 4,677,989 A | * | 7/1987 | Robblee | 607/116 |
| 4,784,161 A | * | 11/1988 | Skalsky et al. | 607/116 |
| 5,267,564 A | * | 12/1993 | Barcel et al. | 600/310 |
| 5,609,611 A | * | 3/1997 | Bolz et al. | 607/13 |
| 5,683,443 A | * | 11/1997 | Munshi et al. | 607/121 |
| 5,935,158 A | * | 8/1999 | Holmstrom et al. | 607/116 |
| 6,298,272 B1 | | 10/2001 | Peterfeso et al. | |
| 6,606,523 B1 | * | 8/2003 | Jenkins | 607/133 |
| 6,799,076 B2 | * | 9/2004 | Gelb et al. | 607/121 |
| 2002/0038134 A1 | | 3/2002 | Greenberg et al. | |

(Continued)

FOREIGN PATENT DOCUMENTS

DE    35 18317 A1    11/1986

(Continued)

OTHER PUBLICATIONS

D. F. Gibbs and B. W. Jones, A capacitance enhancement resulting from the interaction of platinum with the alkali halides, May 19, 1969, J. Phys. C (solid St. Phys.), ser. 2, vol. 2, printed in Great Britain, pp. 1392-1396.*

(Continued)

*Primary Examiner*—George Manuel
(74) *Attorney, Agent, or Firm*—Panitch Schwarze Belisario & Nadel LLP

(57) ABSTRACT

A stimulation electrode is provided having an electrically conducting electrode base member which is partially covered with an electrically insulating ceramic layer. The ceramic layer is formed of an oxide and/or an oxynitride of at least one metal of the group of titanium, niobium, tantalum, zirconium, aluminum and silicon. Various methods are provided for production of the stimulation electrode, including methods in which the ceramic layer is formed in situ by a thermal, chemical or electrochemical oxidation or oxynitridation process. The stimulation electrode may be used as a cardiac pacemaker electrode, a neuro-stimulation electrode, or another human implant.

15 Claims, 4 Drawing Sheets

U.S. PATENT DOCUMENTS

2003/0087197 A1* 5/2003 Schulman et al. ........... 430/315

FOREIGN PATENT DOCUMENTS

| DE | 37 39 826 A1 | 7/1988 |
| DE | 41 12 936 A1 | 10/1991 |
| DE | 693 29 919 T2 | 5/2001 |
| DE | 196 45 162 C2 | 8/2001 |
| EP | 0 054 781 B1 | 10/1984 |
| EP | 0 620 024 B1 | 3/1997 |
| EP | 1 169 972 A1 | 1/2002 |
| WO | WO 98/31419 A1 | 7/1999 |

OTHER PUBLICATIONS

Schaldach, M., et al., "Titannitrid-Herzschrittmacher-Elektroden: Pacemaker Electrodes Made of Titanium Nitride," Biomedizinische Technik, vol. 34, pp. 185-190 (1989).

Riedmüller, J., et al., "Improvement of Stimulation and Sensing Performance of Bipolar Pacemaker Leads," IEEE, pp. 2364-2365 (Feb. 1992).

* cited by examiner

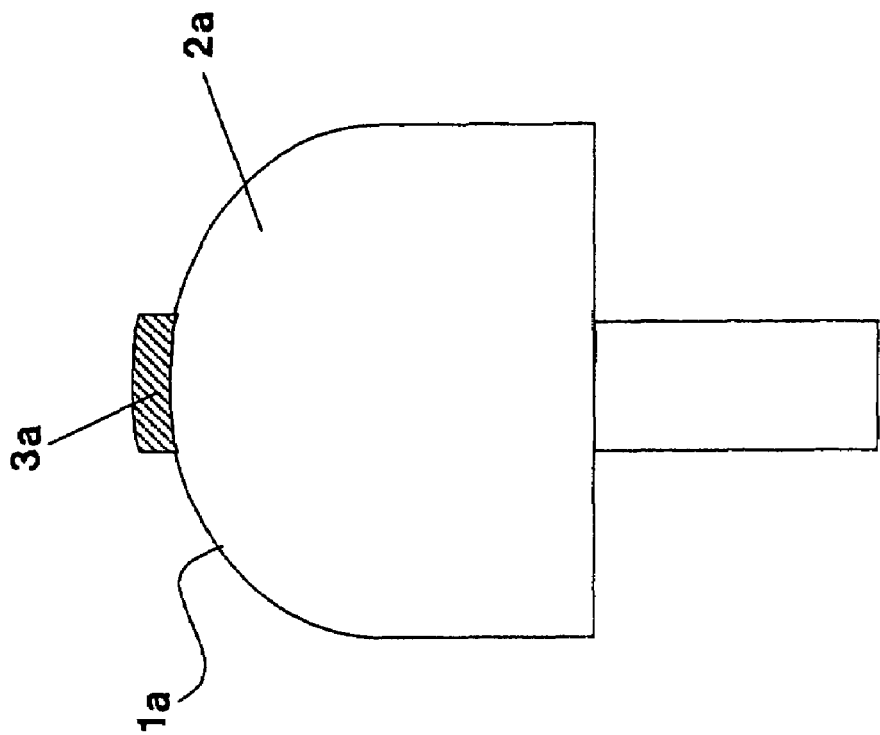
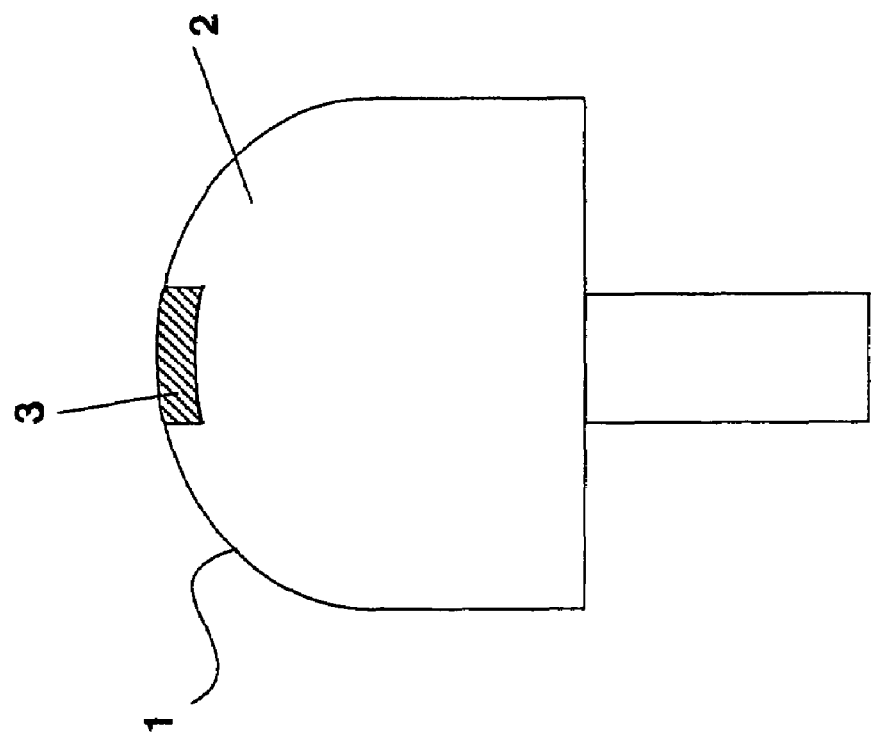
Fig. 1
Fig. 2

STIMULATION ELECTRODE AND METHODS OF MAKING AND USING SAME

BACKGROUND OF THE INVENTION

The invention is directed to a stimulation electrode with an electrically conducting electrode base member, which is partially covered with an electrically insulating ceramic layer, wherein the ceramic layer is formed from an oxide and/or an oxynitride of at least one of the metals selected from the group of titanium, niobium, tantalum, zirconium, aluminum, and silicon. The invention is further directed to the production of such a stimulation electrode and the use of such a stimulation electrode.

European published patent application EP 1 169 972 A1 discloses a catheter, which is equipped with a stimulation electrode. An electrically insulating and thermally conductive layer is arranged in the region of the stimulation electrode and can be formed of ceramic, among other things. The thickness of the electrically insulating and thermally conductive layer is <10 µm.

European Patent EP 0 620 024 B1 discloses stimulation electrode, which has a high-ohmic insulating layer on the electrode tip. A diamond-like carbon, which is extremely biocompatible, is particularly preferred here. The diamond-like carbon can be deposited using a laser, among other things. It is furthermore disclosed that the entire electrode head may be coated with a diamond-like carbon layer and thereafter the stimulation surfaces may be freed, as desired, by photoetching.

U.S. Pat. No. 6,298,272 B1 discloses a cardiac pacemaker electrode, which is provided with an insulating coating in the region of the electrode tip. The insulating coating here can be formed, for example, by dipping, printing, spraying on, painting on, and resist techniques.

International patent application publication WO 98/31419 discloses a cardiac pacemaker electrode, in which the electrode tip has an annular, electrically insulating sheathing. Plastics or elastomers, particularly silicone rubber, are disclosed here as materials for this sheathing.

German published patent application DE 35 18 317 A1 discloses a stimulation electrode, which is partially coated with insulating material. Plastic is disclosed here as the coating material.

BRIEF SUMMARY OF THE INVENTION

The invention now has as an object the provision of a stimulation electrode with very good biocompatibility and high long-term corrosion resistance and which at the same time can be produced rapidly and inexpensively.

The object is attained for the stimulation electrode set forth at the outset in that the electrode base member is further coated, at least partially, with an electrically conducting layer of titanium nitride, niobium nitride, tantalum nitride, zirconium nitride, aluminum nitride, silicon nitride, vanadium nitride, iridium oxide, or an alloy of platinum and iridium, wherein the iridium portion of the alloy is $\geq 21$ wt. % and the platinum portion of the alloy is $\geq$ about 100 ppm.

These materials have a particularly good biocompatibility and can be applied with excellent adhesion to electrically conducting electrode base members. The following description of suitable production methods for the ceramic layer shows that these materials can be used in a simple and inexpensive manner.

In particular, it has been found to be advantageous if the electrode base member here is formed of titanium, tantalum, gold, carbon, platinum, iridium, a platinum-iridium alloy, an alloy based on cobalt and/or nickel, or stainless steel.

The ceramic layer can then be applied on the electrically conducting layer. However, the ceramic layer can also be applied adjacent to the electrically conducting layer on the electrode base member.

It has furthermore been found advantageous to coat the electrode base member, at least partially, with an electrically conducting layer of titanium nitride or with a titanium nitride layer. The ceramic layer here can then be applied both on the electrically conducting layer of titanium nitride and also adjacent the electrically conducting layer of titanium nitride on the electrode base member.

It is advantageous here if the electrically conducting layer of titanium nitride is at least partially covered with at least one oxidation protection layer on its side facing away from the electrode base member. This is of particular advantage when the stimulation electrode is to be used with anodic polarity, since the long-term durability of the stimulation electrode is significantly increased thereby.

The ceramic layer here can be applied on the at least one oxidation protection layer, or instead adjacent the electrically conducting layer of titanium nitride, and the at least one oxidation protection layer can be applied on the electrode base member.

It is furthermore possible for the ceramic layer to be applied adjacent the at least one oxidation protection layer on the electrically conducting layer of titanium nitride.

It has been found to be particularly advantageous for the at least one oxidation protection layer to be formed from at least one element of the group platinum, iridium, and gold. However, it is also possible to form the oxidation protection layer of an oxide, a carbide, a nitride, or a polymer, wherein the at least one oxidation protection layer reduces the impedance electrode base member coated with the electrically conducting layer of titanium nitride, or at most increases it to a value which is smaller than the impedance of the uncoated electrode base member.

The thickness of the oxidation protection layer is advantageously in the range of about 500 nm to about 5 µm.

Thicknesses of about 1 nm to about 20 µm have been found to be advantageous for the ceramic layer; wherein the layer thickness depends heavily on the production method used for forming the ceramic layer.

The ceramic layer can have a surface which is closed in itself or instead can be formed by plural independent surfaces.

The object is attained for a first method of manufacture of the stimulation electrode in that the ceramic layer is formed by a PVD (physical vapor deposition) method, a CVD (chemical vapor deposition) method, or a dip, spray, or sol-gel method. As suitable PVD methods, for example, cathode sputtering, thermal vaporization, electron beam vaporization, or arc vaporization may be considered.

The object is attained for a second method of production of the stimulation electrode, in that the ceramic layer is formed by depositing a metallic layer of titanium and/or niobium and/or tantalum and/or zirconium and/or aluminum and/or silicon, and in that a thermal or electrochemical or chemical oxidation or oxynitriding of the metallic layer subsequently takes place. This method can be performed particularly simply and cost-effectively.

The object is attained for a third method of production of a stimulation electrode with a titanium electrode base member, in that the ceramic layer is formed by the electrode base member being partially oxidized, thermally or chemically, to titanium oxide.

The object is attained for a fourth method of production of a stimulation electrode with a tantalum electrode base member, in that the ceramic layer is formed by the electrode base member being partially oxidized, thermally or chemically, to tantalum oxide.

The third and fourth methods according to the invention make possible the direct formation of the ceramic layer from the material of the electrode base member, so that a separate application of material for the ceramic layer is not required.

The object is attained for a fifth method of production of a stimulation electrode, in which the electrode base member is at least partially covered with an electrically conducting layer of titanium nitride, in that the ceramic layer is formed by the electrically conducting layer of titanium nitride being partially oxidized, thermally or electrochemically, to titanium oxide, wherein the oxidation comprises at least a portion of the layer thickness of the electrically conducting layer of titanium nitride.

For the second through fifth methods according to the invention, it has been found to be particularly advantageous to perform the thermal oxidation with a laser.

For the first through fifth methods according to the invention, it has further been found to be advantageous if the ceramic layer is first formed over the full surface on the uncoated or coated electrode base member, and it is then partially removed again by etching.

The use of the stimulation electrode according to the invention is ideal as a cardiac pacemaker electrode, neuro-stimulation electrode, retinal implant, cochlear implant, or in another human implant.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is a schematic side view of an electrode base member made of titanium with a ceramic layer;

FIG. 2 is a schematic side view of an electrode base member made of stainless steel with a ceramic layer;

DETAILED DESCRIPTION OF THE INVENTION

Figure 4:
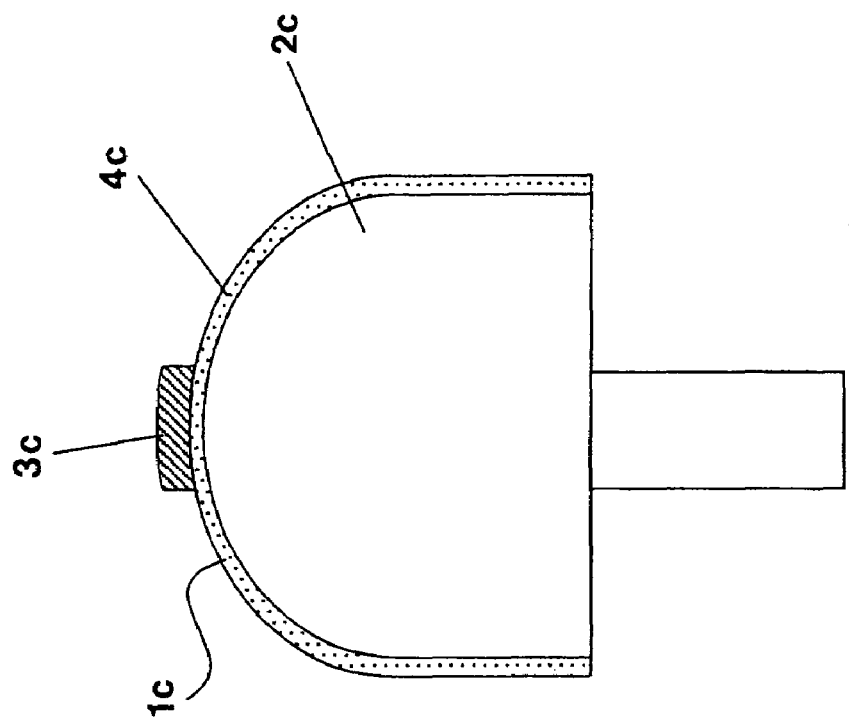
FIG. 4 is a schematic side view, partially in section, of a stimulation electrode according to the invention with a platinum-iridium alloy electrode base member.

FIG. 1 shows an intermediate product 1 in the production of the stimulation electrode according to the invention with a titanium electrode base member 2, which was superficially oxidized by a laser to a ceramic layer 3 of titanium oxide.

FIG. 2 shows and intermediate product 1a in the production of the stimulation electrode according to the invention with a stainless steel electrode base member 2a. A ceramic layer 3a of aluminum oxide, formed by electron beam vaporization, is applied on the electrode base member 2a.

Figure 3:
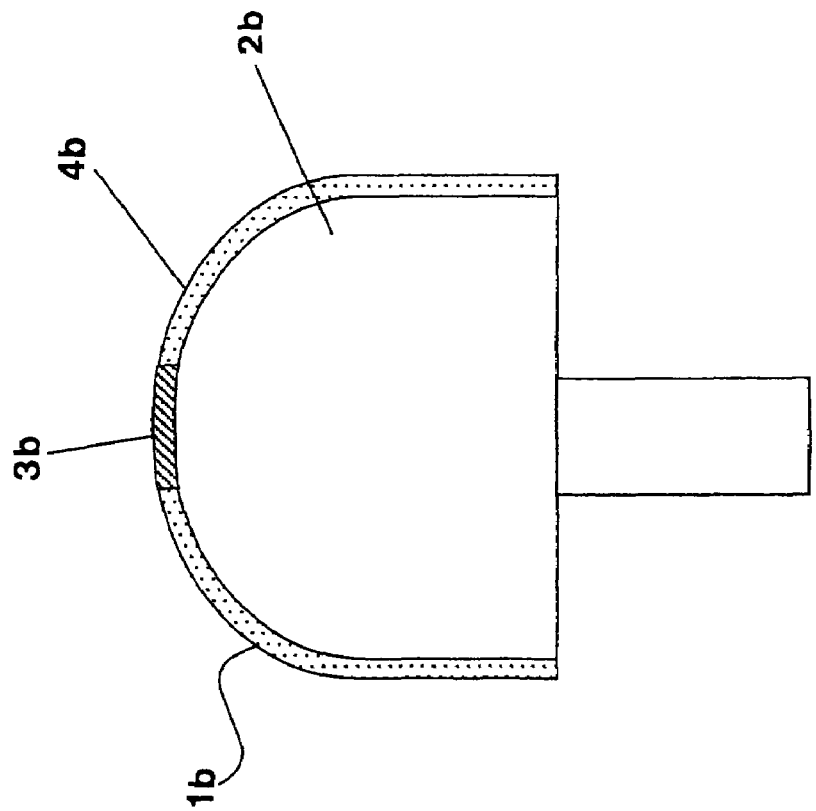
FIG. 3 is a schematic side view, partially in section, of a stimulation electrode according to the invention with a titanium electrode base member having a titanium nitride coating.

FIG. 3 shows a stimulation electrode 1b with a titanium electrode base member 2b. The electrode base member 2b here is coated with a titanium nitride layer 4b. The titanium nitride layer 4b was partially oxidized by electrochemical oxidation to titanium oxide with formation of the ceramic layer 3b.

FIG. 4 shows a stimulation electrode 1c with an electrode base member 2c of a platinum-iridium alloy with 10 wt. % iridium content. The electrode base member 2c here is covered with a layer 4c of iridium oxide. A ceramic layer 3c of tantalum oxide is applied on the layer 4c and was formed by the vapor deposition of metallic tantalum and subsequent thermal oxidation of the tantalum.

Figure 5:
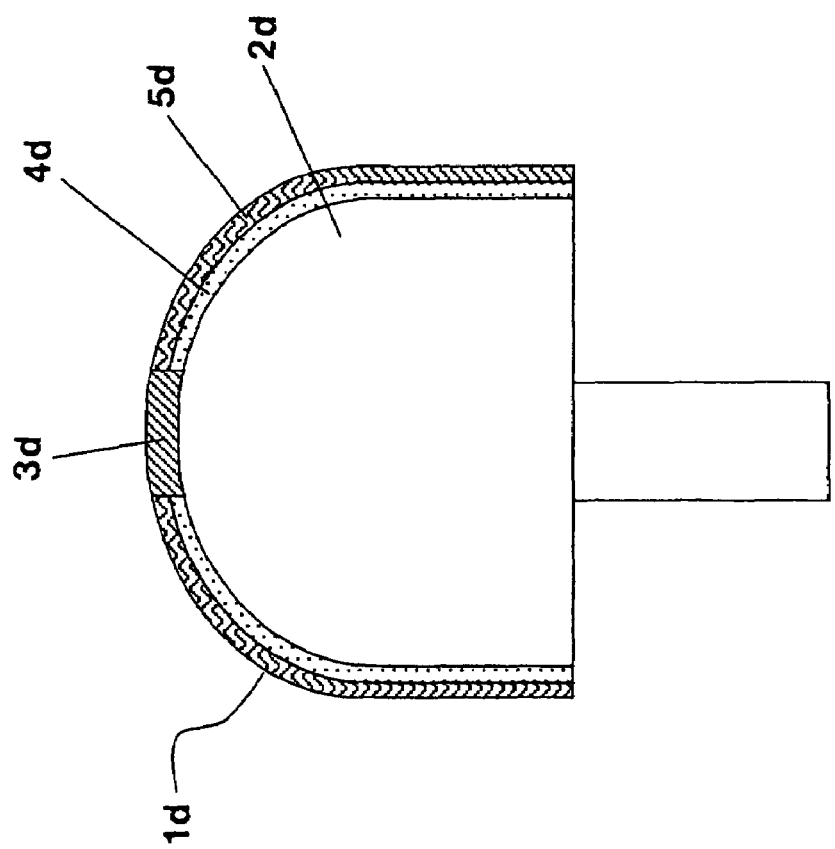

FIG. 5 shows a stimulation electrode 1d with a titanium electrode base member 2d. The electrode base member 2d is covered with a titanium nitride layer 4d, which in turn is overcoated with an iridium oxidation protection layer 5d. A titanium oxide ceramic layer 3d, applied directly on the electrode base member 2d, is arranged adjacent to the titanium nitride layer 4d and also the iridium oxidation protection layer 5d. The ceramic layer 3d here is formed of titanium oxide, which was formed by application of metallic titanium and subsequent thermal oxidation by a laser.

Figure 6:
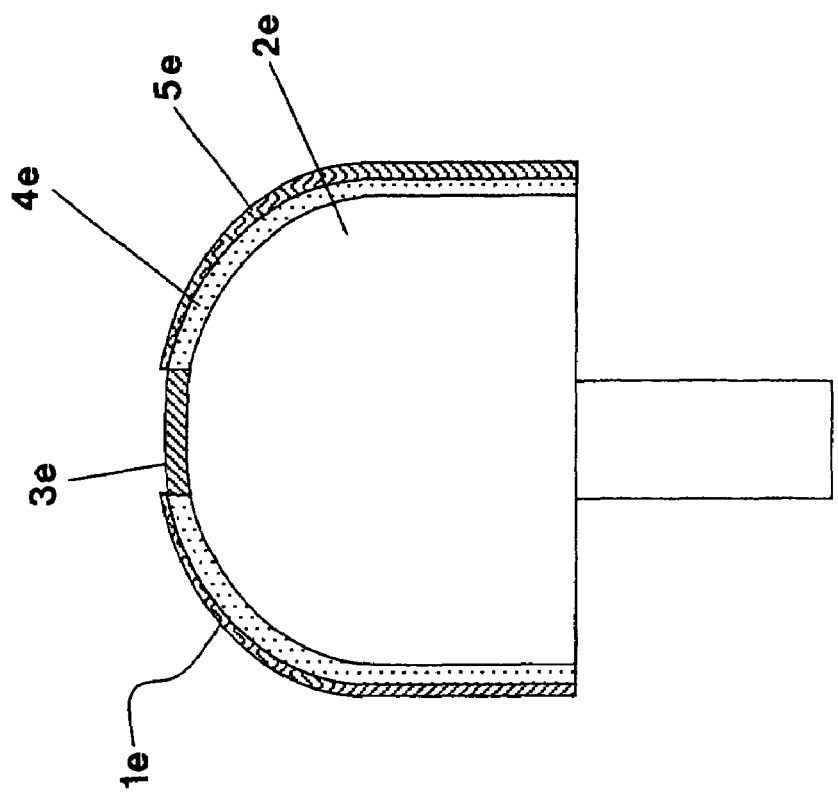
FIGS. 5-8 are schematic side views, partially in section, of stimulation electrodes according to the invention with a titanium electrode base member having a titanium nitride coating and an oxidation protection layer.

FIG. 6 shows a stimulation electrode 1e with a titanium electrode base member 2e. The electrode base member 2e here is covered with a titanium nitride layer 4e, which in turn is partially covered with a platinum oxidation protection layer 5e. In the region in which the oxidation protection layer 5e does not cover the titanium nitride layer 4e, a titanium oxide ceramic layer 3e is formed by oxidation of the titanium nitride layer 4e.

Figure 7:
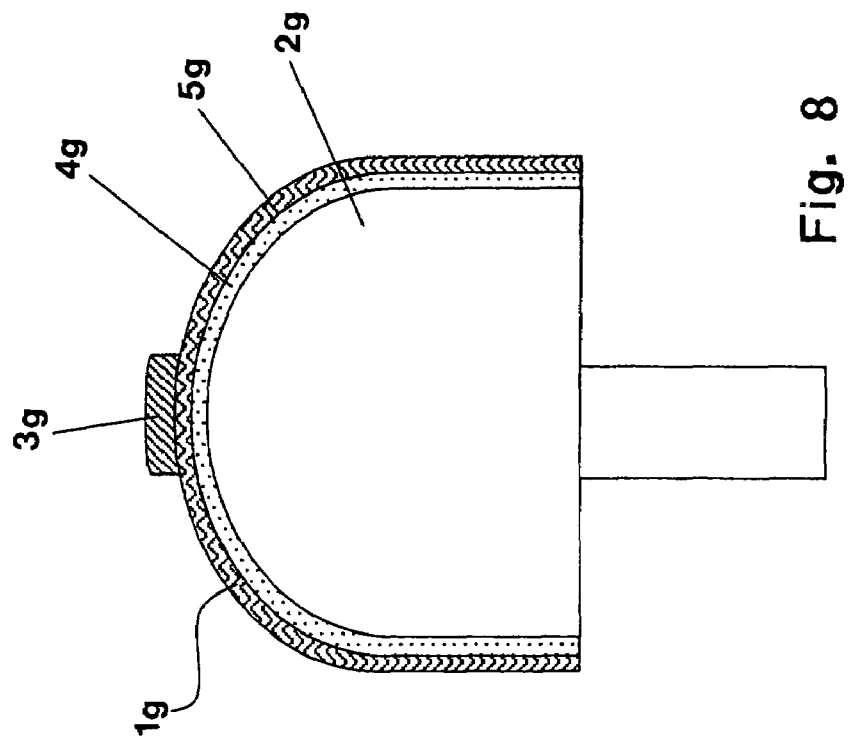

FIG. 7 shows a stimulation electrode 1f with a titanium electrode base member 2f, which is coated with a titanium nitride layer 4f. The titanium nitride layer 4f is partially coated with an iridium oxidation protection layer 5f. In the regions of the titanium nitride layer 4f not covered with the oxidation protection layer 5f, the titanium nitride layer 4f is superficially converted into a titanium oxide ceramic layer 3f by thermal oxidation with a laser.

Figure 8:
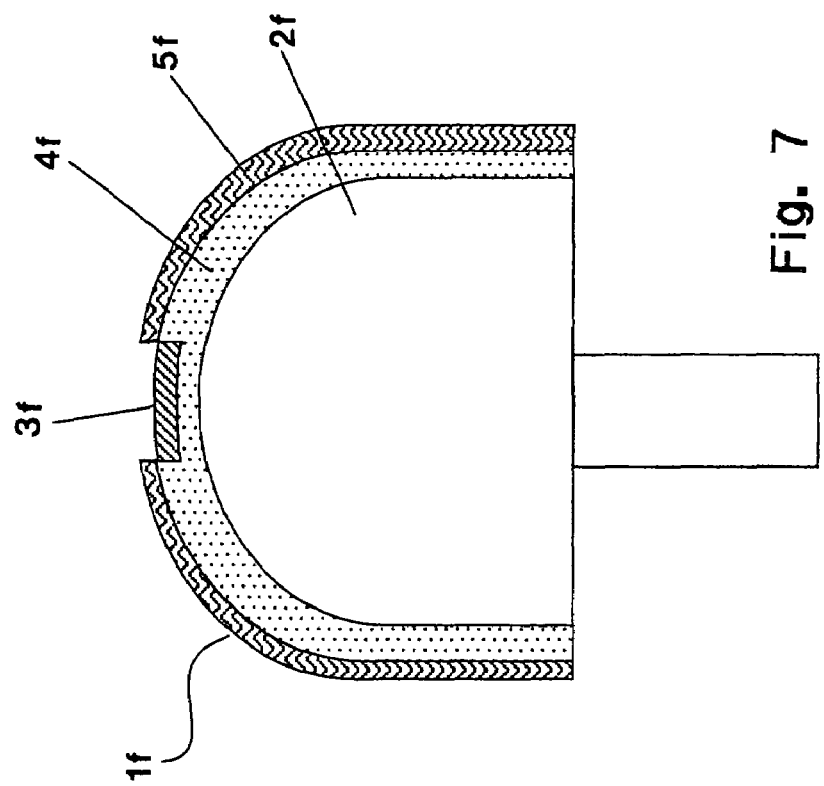

FIG. 8 shows a stimulation electrode 1g with a titanium electrode base member 2g, which is covered with a titanium nitride layer 4g. The titanium nitride layer 4g is further covered with a platinum-iridium alloy oxidation protection layer 5g. A ceramic layer 3g of zirconium oxide, formed by a CVD method, is applied on the oxidation protection layer 5g.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A stimulation electrode comprising an electrically conducting electrode base member (2, 2a, 2b, 2c, 2d, 2e, 2f, 2g) formed of at least one metal selected from the group consisting of gold, carbon, platinum, iridium, platinum-iridium alloys, and stainless steel, wherein the electrode base member is partially covered with an electrically insulating ceramic layer, wherein the ceramic layer (3, 3a, 3b, 3c, 3d, 3e, 3f, 3g) has a thickness of about 1 nm to about 20 µm and is formed of an oxide and/or an oxynitride of at least one metal selected from the group consisting of titanium, niobium, tantalum, zirconium, aluminum, and silicon, and wherein the electrode base member (2, 2a, 2b, 2c, 2d, 2e, 2f, 2g) is further at least partially coated with and in direct contact with an electrically conducting layer (4b, 4c, 4d, 4e, 4f, 4g) comprising at least one material selected from the group consisting of titanium nitride, niobium nitride, tantalum nitride, zirconium nitride, aluminum nitride, silicon nitride, vanadium nitride, iridium oxide, and an alloy of platinum and iridium, wherein the iridium portion of the alloy is ≧21 wt. % and the platinum portion of the alloy is ≧ about 100 ppm.

2. The stimulation electrode according to claim 1, wherein the ceramic layer (3, 3a, 3b, 3c, 3d, 3e, 3f, 3g) is arranged on the electrically conducting layer (4c).

3. The stimulation electrode according to claim 1, wherein the ceramic layer (3, 3a, 3b, 3c, 3d, 3e, 3f, 3g) is arranged adjacent the electrically conducting layer on the electrode base member (2, 2a, 2b, 2c, 2d, 2e, 2f, 2g).

4. The stimulation electrode according to claim 1, wherein the electrically conducting layer (4b, 4d, 4e, 4f, 4g) is formed of titanium nitride.

5. The stimulation electrode according to claim 4, wherein the electrically conducting layer (4b, 4d, 4e, 4f, 4g) of titanium nitride is at least partially covered with at least one oxidation protection layer (5d, 5e, 5f, 5g) on its side facing away from the electrode base member (2, 2a, 2b, 2c, 2d, 2e, 2f, 2g).

6. The stimulation electrode according to claim 5, wherein the ceramic layer (3, 3a, 3b, 3c, 3d, 3e, 3f, 3g) is arranged on the at least one oxidation protection layer (5d, 5e, 5f, 5g).

7. The stimulation electrode according to claim 5, wherein the ceramic layer (3, 3a, 3b, 3c, 3d, 3e, 3f, 3g) is arranged adjacent the electrically conducting layer (4d, 4e, 4f, 4g) of titanium nitride and the at least one oxidation protection layer (5d, 5e, 5f, 5g) on the electrode base member (2, 2a, 2b, 2c, 2d, 2e, 2f, 2g).

8. The stimulation electrode according to claim 5, wherein the ceramic layer (3, 3a, 3b, 3c, 3d, 3e, 3f, 3g) is arranged adjacent to the at least one oxidation protection layer (5d, 5e, 5f, 5g) on the electrically conducting layer (4b, 4d, 4e, 4f, 4g) of titanium nitride.

9. The stimulation electrode according to claim 5, wherein the oxidation protection layer (5d, 5e, 5f, 5g) is formed of at least one element selected from the group consisting of platinum, iridium, and gold.

10. The stimulation electrode according to claim 5, wherein the oxidation protection layer (5d, 5e, 5f, 5g) is formed of at least one compound selected from the group consisting of oxides, carbides, nitrides, and polymers, and wherein the at least one oxidation protection layer (5d, 5e, 5f, 5g) reduces the impedance of the electrode base member (2, 2a, 2b, 2c, 2d, 2e, 2f, 2g) coated with the electrically conducting layer (4d, 4e, 4f, 4g) of titanium nitride, or at most increases the impedance to a value which is smaller than the impedance of the uncoated electrode base member (2, 2a, 2b, 2c, 2d, 2e, 2f, 2g).

11. The stimulation electrode according to claim 5, wherein the oxidation protection layer (5d, 5e, 5f, 5g) has a thickness in a range of about 500 nm to about 5 μm.

12. The stimulation electrode according to claim 1, wherein the ceramic layer (3, 3a, 3b, 3c, 3d, 3e, 3f, 3g) has a surface closed in itself.

13. The stimulation electrode according to claim 1, wherein the ceramic layer (3, 3a, 3b, 3c, 3d, 3e, 3f, 3g) has plurality of independent surfaces.

14. The stimulation electrode according to claim 1, wherein the electrode is implantable in a human.

15. The stimulation electrode according to claim 14, wherein the electrode is implanted as a cardiac pacemaker electrode or a neuro-stimulation electrode.

* * * * *